(12) United States Patent
Okabe (10) Patent No.: US 6,643,395 B1
(45) Date of Patent: Nov. 4, 2003

(54) DEFECT INFORMATION PROCESSING APPARATUS AND METHOD

(75) Inventor: Masaharu Okabe, Tsuchiura (JP)

(73) Assignee: Canon Kabushiki Kaisha (JP)

( * ) Notice: Subject to any disclaimer, the term of this patent is extended or adjusted under 35 U.S.C. 154(b) by 680 days.

(21) Appl. No.: 09/597,142

(22) Filed: Jun. 20, 2000

(30) Foreign Application Priority Data

Jun. 24, 1999 (JP) ............................................ 11-178873

(51) Int. Cl.$^7$ .................................................. G06K 9/00

(52) U.S. Cl. ........................................ 382/149; 382/260

(58) Field of Search ................................ 382/141, 143, 382/144, 149, 147, 260, 261, 262, 263, 264

(56) References Cited

U.S. PATENT DOCUMENTS 6,335,982 B1 * 1/2002 Arai et al. ................... 382/149

* cited by examiner

Primary Examiner—Bhavesh M. Mehta
Assistant Examiner—Ali Bayat
(74) Attorney, Agent, or Firm—Fitzpatrick, Cella, Harper & Scinto (57) ABSTRACT

A two-dimensional image of an object to be inspected is captured, and is converted into multi-valued digital data by an A/D converter (2). A vertical filter (4) computes difference values of the multi-valued digital image data in units of pixels within a predetermined range in the vertical direction, and a horizontal filter (5) computes difference values in the horizontal direction based on the difference values computed by the vertical filter (4). A binary converter (7) converts the difference values computed by the horizontal filter (5) into binary data on the basis of a predetermined reference value. A defect portion of the object to be inspected is detected based on the multi-valued digital data as the difference values computed by the horizontal filter (5), and binary data.

24 Claims, 7 Drawing Sheets

DEFECT INFORMATION PROCESSING APPARATUS AND METHOD

FIELD OF THE INVENTION

The present invention relates to a defect information processing apparatus and method for capturing an image on the cylindrical surface of, e.g., a photosensitive drum or the like, and detecting defect information that pertains to smoothness or uniformity from the captured image data.

BACKGROUND OF THE INVENTION

In recent years, the resolutions of images formed by copying machines and the like and those displayed on liquid crystal displays and the like have become higher beyond that of the human eye. Along with the advance of such technique, small defects present on the surface of a photosensitive drum, developing sleeve, liquid crystal display board, or dedicated printing paper used in the copying machines, printers, or the like have serious influences on higher resolutions. Also, a defect itself to be detected becomes very smaller as the resolution becomes higher.

Figure 7:
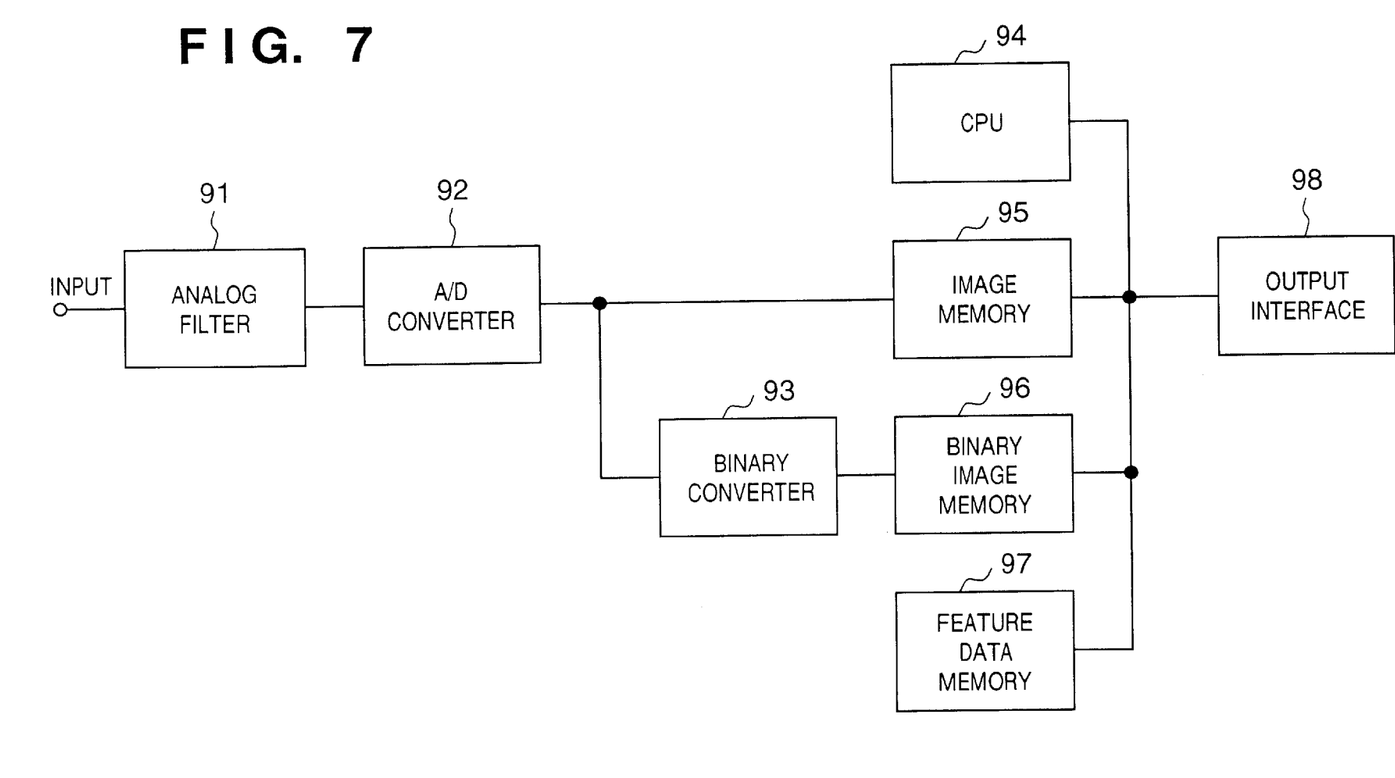
FIG. 7 is a circuit block diagram of a conventional defect information processing apparatus.

FIG. 7 is a circuit block diagram of a conventional defect information processing apparatus.

As shown in FIG. 7, a conventional defect information processing apparatus scans the surface to be inspected of an object under inspection with a laser beam, and inputs an analog image of the surface to be inspected by a light receiver. From the analog image, unnecessary frequency components are removed by an analog filter 91, and that image is converted from an analog signal into a digital signal via an A/D converter 92. The image data is stored as multi-valued image data in an image memory 95. Also, the image data is converted into a binary signal via a binary converter 93 and the binary signal is stored in a binary image memory 96.

A CPU 94 computes defect data corresponding to a certain defect on the surface to be inspected on the basis of the multi-valued image data stored in the image memory 95, and the binary signal stored in the binary image memory 96, and stores, as feature data, the maximum and minimum values, the number of pixels, the coordinates, and the like of the defect data in a feature data memory 97. The CPU 94 checks based on the feature data stored in the feature data memory 97 if the object to be inspected is defective, and displays the checking result on a CRT or the like via an output interface 98.

However, since the filter used in the conventional apparatus is effective only for an image in the main scan direction of the laser beam due to its time-serial operation, if no change is found in the detection signal in the main scan direction, defect data cannot be obtained via the analog filter. For example, when an aluminum photosensitive drum is prepared by drawing, and a defect such as a thin scratch is formed in the longitudinal direction of the cylindrical surface of the drum, since nearly no change is detected in the detection signal even by scanning in the longitudinal direction (main scan direction) of the drum, the defect can hardly be detected.

In order to solve this problem, when a two-dimensional spatial filter is used, and the filter size for the sib-scan direction of a laser beam is set to be 5 lines or more, the hardware scale and cost increase, and DSP software processes are slow.

SUMMARY OF THE INVENTION

The present invention has been made in consideration of the aforementioned problems and has as its first object to provide a defect information processing apparatus and method which can form a large-size filter by a simple circuit, and can achieve a cost reduction and high-speed processes.

It is the second object of the present invention to provide a defect information processing apparatus and method which can further increase the filter size, and can improve the defect detection performance.

It is the third object of the present invention to provide a defect information processing apparatus and method which can form an arithmetic device by a simple circuit, and can achieve high-speed processes.

In order to solve the aforementioned problems and to achieve the above objects, a defect information processing apparatus of the present invention comprises the following means. That is, there is provided a defect information processing apparatus comprising:

image input means for capturing a two-dimensional image of an object to be inspected;

digital conversion means for converting the two-dimensional image into multi-valued digital image data;

vertical filter means for filtering the multi-valued digital image data in a vertical direction;

horizontal filter means for filtering the multi-valued digital image data, which has been filtered by the vertical filter means, in a horizontal direction;

binarization means for converting the multi-valued digital image data, which has been filtered by the horizontal filter means, into binary data on the basis of a predetermined reference value; and detection means for detecting a defect portion of the object to be inspected on the basis of the multi-valued digital image data and binary data, wherein the vertical filter means comprises vertical difference computation means for computing a difference value of the multi-valued digital image data within a predetermined range in the vertical direction, and vertical weighting means for weighting the difference value computed by the vertical difference computation means, and the horizontal filter means comprises horizontal difference computation means for computing a difference value of the multi-valued digital image data within a predetermined range in the horizontal direction, and horizontal weighting means for weighting the difference value computed by the horizontal difference computation means.

A defect information processing method of the present invention comprises the following steps. That is, there is provided a defect information processing method comprising:

the image input step of capturing a two-dimensional image of an object to be inspected;

the digital conversion step of converting the two-dimensional image into multi-valued digital image data;

the vertical filter step of filtering the multi-valued digital image data in a vertical direction;

the horizontal filter step of filtering the multi-valued digital image data, which has been filtered in the vertical filter step, in a horizontal direction;

the binarization step of converting the multi-valued digital image data, which has been filtered in the horizontal filter step, into binary data on the basis of a predetermined reference value; and the detection step of detecting a defect portion of the object to be inspected on the basis of the multi-valued digital image data and binary data, wherein the vertical filter step comprises the vertical difference computation step of computing a difference value of the multi-valued digital image data within a predetermined range in the vertical direction, and the vertical weighting step of weighting the difference value computed in the vertical difference computation step, and the horizontal filter step comprises the horizontal difference computation step of computing a difference value of the multi-valued digital image data within a predetermined range in the horizontal direction, and the horizontal weighting step of weighting the difference value computed in the horizontal difference computation step.

As described above, according to the present invention, even for a defect that changes slightly in the main scan direction, a large detection signal can be obtained by providing digital filters having large numbers of taps in the horizontal and vertical directions.

By satisfying the required filter function while suppressing the circuit scale of the filter process in the main scan direction, the defect detection performance can be improved, and the apparatus cost can be reduced.

Since the number of stages of the filter process is not limited, the performance for emphasizing a defect signal improves.

Therefore, the quality guarantee precision of products inspected using the apparatus and method of the present invention can be improved, and the manufacturing cost can be reduced.

Other objects and advantages besides those discussed above shall be apparent to those skilled in the art from the description of a preferred embodiment of the invention which follows. In the description, reference is made to accompanying drawings, which form a part thereof, and which illustrate an example of the invention. Such example, however, is not exhaustive of the various embodiments of the invention, and therefore reference is made to the claims which follow the description for determining the scope of the invention.

DETAILED DESCRIPTION OF THE PREFERRED EMBODIMENTS

The preferred embodiments of the present invention will now be described in detail with reference to the accompanying drawings.

First Embodiment

A defect information processing apparatus of the first embodiment will be explained below with reference to FIG. 1.

Figure 1:
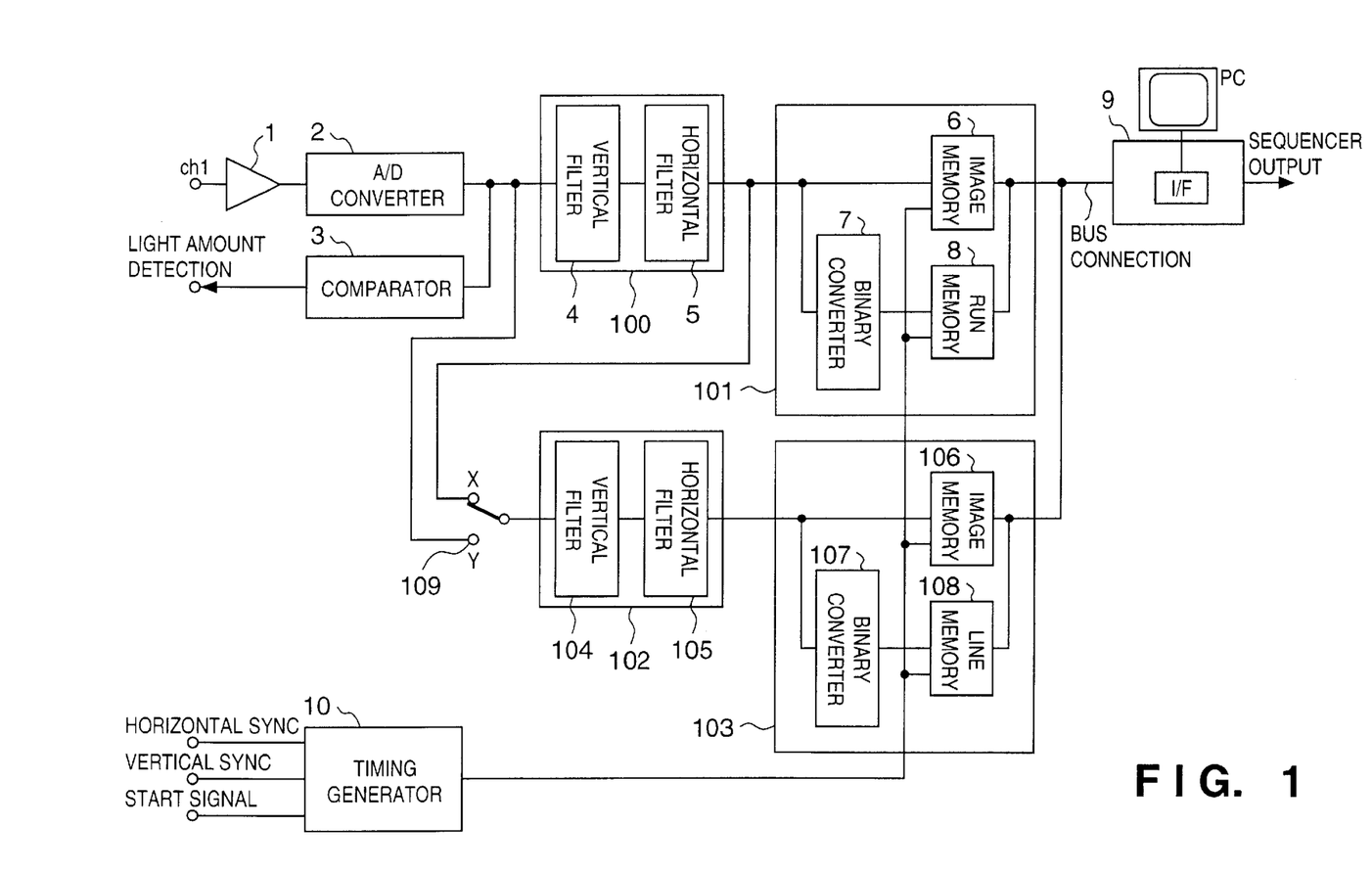
FIG. 1 is a circuit block diagram of a defect information processing apparatus according to the first embodiment of the present invention.

FIG. 1 is a circuit block diagram showing a defect information processing apparatus according to the first embodiment of the present invention.

As shown in FIG. 1, reference numeral 1 denotes an input amplifier; 2, an A/D converter for converting an analog signal into an 8-bit digital signal; 3, a digital comparator; 100 and 102, filter processors; 109, a switch for switching the input to the filter processor 102; 4 and 104, vertical linear filters; 5 and 105, horizontal linear filters; 101 and 103, memories for storing a multi-valued image and binary run code; 6 and 106, image memories for recording 8-bit multi-valued digital image data; 7 and 107, binary converters, each of which binarizes the multi-valued digital image data by comparing it with a predetermined reference value and has a horizontal linear filter function; 8 and 108, run memories for converting and storing a binary signal into a run code; 9, a control computer which segments the run code into run areas on the basis of the multi-valued digital image data stored in the image memories 6 and 106, and the binary signals stored in the run memories 8 and 108, computes maximum and minimum values, areas, coordinates, and the like as feature data of those run areas, and determines a defect if each feature data deviates from a predetermined prescribed value; and 10, a timing generator for generating the operation timings of the individual circuits by receiving horizontal and vertical sync signals and a start signal.

In the above circuit, when the switch 109 is switched to the X side to input the output from the filter processor 100 to the filter processor 102, the input signal can be filtered twice in real time by the filter processors 100 and 102. Also, since arithmetic coefficients can be individually set in the filter processors 100 and 102, a defect can be more emphasized compared to single filtering. Note that the number of stages of the filter processors is not limited to two, and the defect emphasis effect can be improved if the number of stages is increased to three or four.

The mechanical arrangement of the defect information processing apparatus of the first embodiment will be described below with reference to FIGS. 2A and 2B.

Figure 2A:
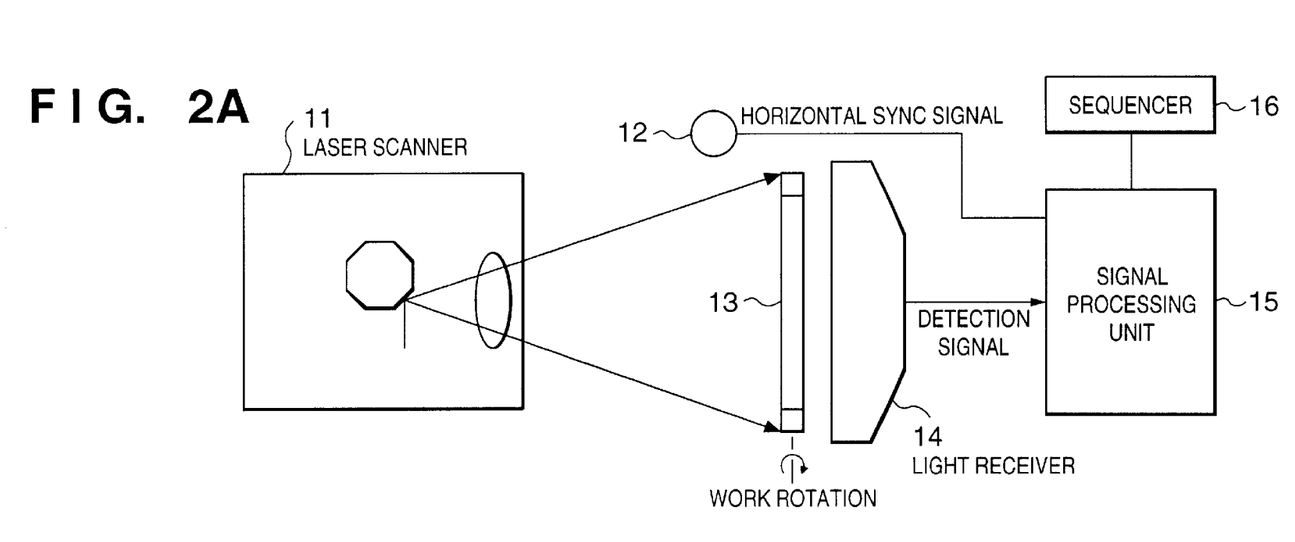
FIG. 2A is a view showing the system arrangement of the defect information processing apparatus according to the first embodiment of the present invention.

FIG. 2A shows the system arrangement of the defect information processing apparatus according to the first embodiment of the present invention. FIG. 2B is a side view of FIG. 2A.

Figure 2B:
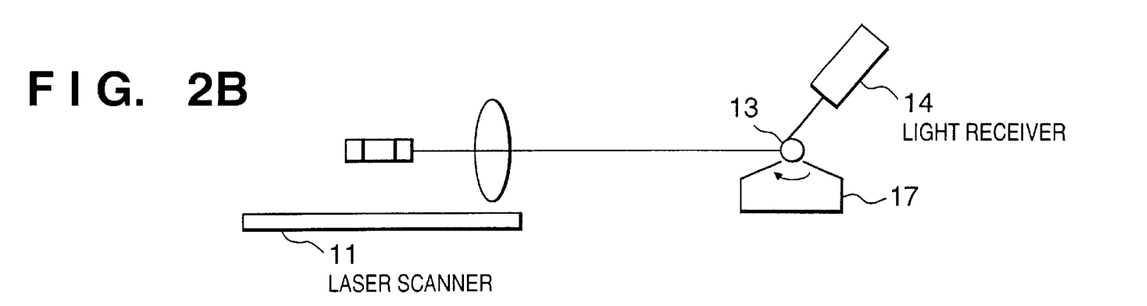
FIG. 2B is a side view of FIG. 2A.

As shown in FIGS. 2A and 2B, reference numeral 11 denotes a laser beam scanner for linearly scanning a laser beam spot having a beam size of around 100 μm; 12, a beam detector for detecting a laser beam; 13, a developing sleeve of a copying machine cartridge as an object to be inspected (to be referred to as a work hereinafter); 14, a light receiver for uniformly receiving light reflected by the entire surface of the work using a photomultiplier; 15, a signal processing unit shown in FIG. 1; 16, a sequencer for controlling the overall apparatus; and 17, a motor & clamp mechanism for scanning in the sub-scan direction by rotating the developing sleeve 13 as the work at constant speed.

Figure 3:
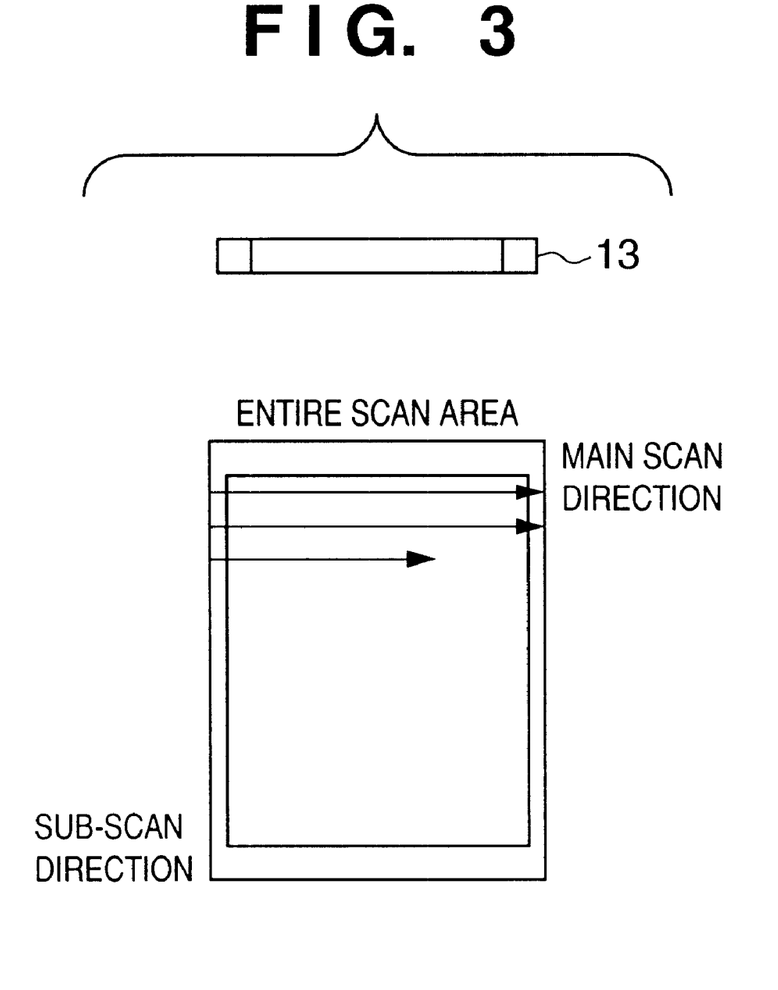
FIG. 3 is a view for explaining a scan area defined by the main scan and sub-scan directions of the first embodiment.

When the entire surface of the work is scanned by the laser scanner 11, the signal detected by the light receiver 14 is expressed as a time-serial, two-dimensional signal, as shown in FIG. 3.

Since the laser beam is scanned along the generator of the developing sleeve, the main scan direction agrees with the longitudinal direction of the sleeve. When the developing sleeve 13 is rotated slowly with respect to the scan period of the laser beam in the main scan direction, a sub-scan can be achieved, and the rotational direction of the developing sleeve 13 agrees with the sub-scan direction.

On the entire scan area, horizontal sampling is done at clocks of 10 MHz, the number of pixels are around 1,000, the length of the work is around 300 mm, and the resolution is around 30 $\mu$m. Also, the work has a diameter of around 12 mm, and is rotated so that scans for 200 lines in the main scan direction amount to one round of the surface of the work. Hence, the resolution per line is around 20 $\mu$m.

Upon scanning the laser beam, the signal processing unit 15 receives the detection signal form the light receiver 14, a horizontal sync signal from the beam detector, and a vertical sync signal from a rotation detector (not shown) for detecting the rotation of the work.

In the signal processing unit 15, the amplitude of the detection signal is adjusted to the input range of the A/D converter 2 by the input amplifier 1, and the detection signal is converted into an 8-bit digital signal by the A/D converter 2. The digital signal is compared with a predetermined value by the comparator 3. If the digital signal is higher than this predetermined value, the digital signal is output, and it is determined that the laser scanner, light receiver, and the like are normal. If the digital signal is lower than the predetermined value, since no digital signal is output, it is determined that the laser scanner, light receiver, or the like has failed. The output signal from the comparator 3 is output to the sequence as a host controller as a light amount detection signal.

When the switch 109 is switched to the Y side, the digital signal undergoes vertical linear filter processes by the vertical filters 4 and 104, and then undergoes horizontal linear filter processes by the horizontal filters 5 and 105. The contents of the filter processes can be arbitrary set. For example, when the vertical filters 4 and 104 are set to compute the difference between the difference values between the closest scan line and 127th line, and those from the 50th to 53rd lines, since they compute the base line of a signal corresponding to a length of around 2 mm, the size of a signal corresponding to a length of around 80 $\mu$m, and their difference, a slow change in signal having a period of 2 mm or more such as an undulation of the work surface can be canceled, and a defect signal of around 80 $\mu$m can be emphasized.

Likewise, by arbitrarily setting the contents of the filter processes of the horizontal filters 5 and 105, the waveform of the signal frequency band to be detected as a defect signal from the filtered signal can be emphasized.

On the other hand, when the switch 109 is switched to the X side, the output from the filter processor 100 is input to the filter processor 102, and the digital signal is filtered twice in real time by the filter processors 100 and 102.

When the vertical filters 4 and 104 are inserted at the input side of the horizontal filters 5 and 105, a defect signal of, e.g., a thin scratch along the main scan direction, which cannot be detected by an analog signal filter process alone, can be emphasized. Therefore, detection errors of defects formed on the work surface can be prevented, thus improving the detection precision.

Figure 4:
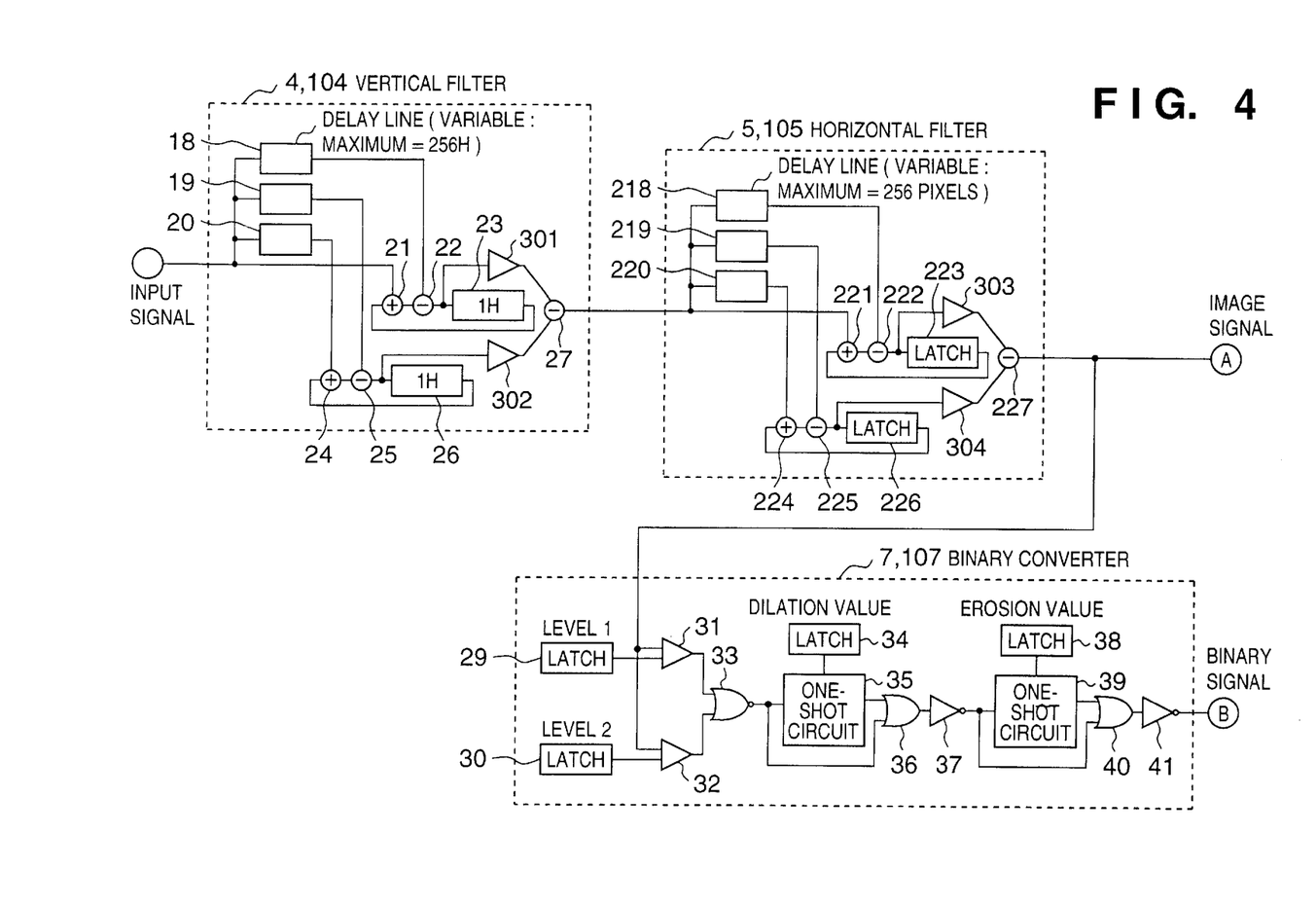
FIG. 4 is a block diagram of a vertical filter, horizontal filter, and binary converter shown in FIG. 1.

FIG. 4 shows details of the vertical filter, horizontal filter, and binary converter shown in FIG. 1.

As shown in FIG. 4, the vertical filters 4 and 104, and horizontal filters 5 and 105 comprise non-cyclic digital filters. The vertical filters 4 and 104 have variable delay lines up to a maximum of 256H, and the horizontal filters 5 and 105 have variable delay lines up to a maximum of 256 pixels.

In FIG. 4, each of the vertical filters 4 and 104 has delay lines 18 to 20 from the closest line to the line three lines before. A vertical difference process of the vertical filter 4 computes the difference (or sum) between the difference values of pixels within the range from the closest line (input signal) to the line three lines before (delay line 18), and those within the range from the line two lines before (delay line 19) and the line one line before (delay line 20). That is, an adder 21 adds the pixel value of the input signal of the closest line to the difference value of one line before, which is stored in a memory 23 having a capacity for one line, and a subtractor 22 subtracts the pixel value added by the adder 21 from that of the line three lines before. Likewise, an adder 24 adds a pixel value one line before to the difference value one line before, which is stored in a memory 26 having a capacity for one line, and a subtractor 25 subtracts the pixel value added by the adder 24 from that two lines before.

The difference value computed by the subtractor 22 is multiplied by a predetermined weight by a multiplier 301, the difference value computed by the subtractor 25 is multiplied by a predetermined weight by a multiplier 302, and a subtractor 27 computes the difference between the values computed by the multipliers 301 and 302 and outputs it to the horizontal filter 5. In each of the vertical filters 4 and 104, when the aforementioned difference computations are continuously done, the memory 23 can always hold the sum total of pixel values within the range from the closest line to a line a predetermined number of lines before (three lines before), and the memory 26 can always hold the sum total of pixel values set between the delay line 20 and the delay line 19.

Since the delay lines 18 to 20 and the memories 23 and 26 for one line are cleared by an initialization signal (not shown), an initial state can be set. After that, the value of the memory 23 for one line becomes effective upon receiving data for a length delayed by the delay line 18.

When the delay line 18 is set to have a larger length, and the difference between the lengths of the delay lines 19 and 20 is set for several lines, since the delay line 18 is long, the sum total within a broad range can be obtained in the memory 23. This value includes a low undulation frequency component by suppressing small changes. On the other hand, since the difference between the delay lines 19 and 20 is as small as several lines, the sum total of several pixels is obtained in the memory 26. This value includes a frequency signal component equal to or lower than high frequency components exceeding the frequency corresponding to the length for several pixels by suppressing such high frequency components. That is, two low-pass filters having different cutoff frequencies can be formed. After the gain adjustment is done in the multipliers 301 and 302 to weight these values, the difference between these values is computed, thus suppressing high frequency components and low undulation frequency components from the output value. That is, a means which implements a sub-scan linear filter process as a whole can be formed, and this filter constructs a band-pass filter.

For this reason, when given delay mounts of the delay lines 18 to 20 are set, and the gain adjustment is done by the multipliers 301 and 302, the vertical filter can be set to have band-pass characteristics that match the size of a defect to be detected. Hence, a required defect signal can be emphasized, and a defect can be easily detected.

Although not shown, by simplifying multiplication circuits of the multipliers 301 and 302, and using a barrel shifter which selects and extracts pixel values within a predetermined range of this computation result, a sum total/$2^n$ can be computed. When the subtractor 27 computes the difference between the pixel values within the two ranges, a computation for removing undulation components of the input signal and emphasizing a defect signal can be implemented.

Likewise, each of the horizontal filters 5 and 105 has delay lines 218 to 220 from the closest pixel to the pixel three pixels before. A horizontal difference process of the horizontal filter computes the difference (or sum) between the difference values of pixels within the range from the closest pixel (input signal from the vertical filter) to the pixel three pixels before (delay line 218), and those within the range from the pixel two pixels before (delay line 219) and the pixel one pixel before (delay line 220). That is, an adder 221 adds the pixel value of the input signal of the closest pixel to the difference value of one line before, which is stored in a latch 223 having a capacity for one word, and a subtractor 222 subtracts the pixel value added by the adder 221 from that of the pixel three pixels before. Likewise, an adder 224 adds a pixel value one pixel before to the difference value one pixel before, which is stored in a latch 226 having a capacity for one word, and a subtractor 225 subtracts the pixel value added by the adder 224 from that two pixels before.

The difference value computed by the subtractor 222 is multiplied by a predetermined weight by a multiplier 303, the difference value computed by the subtractor 225 is multiplied by a predetermined weight by a multiplier 304, and a subtractor 227 computes the difference between the values computed by the multipliers 303 and 304 and outputs it from the horizontal filter 5. In each of the horizontal filters 4 and 104, when the aforementioned difference computations are continuously done, the latch 223 can always hold the sum total of pixel values within the range from the closest pixel to a pixel a predetermined number of pixels before (three pixels before), and the latch 226 can always hold the sum total of pixel values set between the delay line 220 and the delay line 219. Although not shown, by simplifying multiplication circuits of the multipliers 303 and 304, and using a barrel shifter which selects and extracts pixel values within a predetermined range of this computation result, a sum total/$2^n$ can be computed. When the subtractor 227 computes the difference between the pixel values within the two ranges, a computation for removing undulation components of the input signal and emphasizing a defect signal can be implemented.

In the horizontal filter, as in the vertical filter, when predetermined amounts are set in the delay lines 218 to 220, and these delay lines and latches 223 and 226 are cleared by initialization to start operation, effective data are stored in the latches 223 and 226 after data for the length of the delay line is input. In these latches, the sum totals of data according to the delay amounts are obtained as in the vertical filter. With this function, two low-pass filters can be formed, and their difference is used as the output from the horizontal filter. Hence, as in the vertical filter, the horizontal filter can implement a linear filter process, and serves as a band-pass filter.

When given delay mounts of the delay lines 218, 219, and 220 are set, and the gain adjustment is done by the multipliers 303 and 304, the horizontal filter can be set to have band-pass characteristics that match the size of a defect to be detected. Hence, a required defect signal can be emphasized, and a defect can be easily detected.

The binary converter 7 sets two difference reference values for multi-valued digital data which has undergone the difference computation processes of the vertical filter 4 and horizontal filter 5. For example, if the multi-valued digital data output from the horizontal filter 5 falls within the range between the reference values in latches 29 and 30, the binary converter 7 converts that data into a binary signal "0"; if that data falls outside the range, the converter 7 converts the data into a binary signal "1".

In the binary converter 7, the OR of the first reference value of the latch 29 and the multi-valued digital data, and the OR of the second reference value of the latch 30 is input to an OR gate 33. If the multi-valued digital data is larger than the first reference value (the output from a comparator 31 is "1") or is smaller than the second reference value (the output from a comparator 32 is "1"), the output from the OR gate 33 changes to "1"; otherwise, the output from the OR gate 33 changes to "0". The binary output value from the OR gate 33 expands the pulse with of a pixel value="1" in a one-shot circuit 35 having a latch 34 which holds a predetermined dilation value of morphological operation by the number of clocks designated by the latch 34. The pixel value of the output from the one-shot circuit 35 is inverted via an OR gate 36 and inverter 37, and is then output to a one-shot circuit 39 having a latch 38 which holds a predetermined erosion value of morphological operation. The output from the one-shot circuit 39 is inverted again by an OR gate 40 and inverter 41, and is output to the run memory 8 as a binary signal. Since the output value from the one-shot circuit 39 is inverted again by the OR gate 40 and inverter 41, the pulse width of zero pixel value is expanded by the number of clocks designated by the latch 38.

The binary converter 7 implements morphological dilation operation of a horizontal image process by hardware by expanding the pulse width of an output "1" in multi-valued digital data converted into binary data by the comparators 31 and 32. In the next stage, the converter 7 executes erosion operation by similarly expanding the pulse width of zero level of a binary signal. In this manner, with this dilation operation, even when a signal is disturbed by, e.g., mixed noise, and defect detection signals which indicate a single defect are separately detected, nearby detection signals can be coupled to obtain an original, single detection signal, and detection data which is faithful to a defect on the actual work surface can be obtained. In this manner, the number of defect positions, which may be repetitively counted by the conventional apparatus due to noise, can be accurately detected.

Since the binary converter also has an erosion operation function, an isolated detection signal having a small width can be erased as noise, thus reducing detection errors of defects.

The stored data is read out by the CPU, and undergoes a software defect detection process.

When a vertical filter having an arbitrary shape is to be formed, the circuit scale increases, resulting in high cost. Hence, the function is limited to only a filter constant suitable for defect detection to reduce the circuit scale, and to provide an arrangement having a satisfactory function.

Also, the horizontal filter can use the same arrangement as that of the vertical filter. The delay lines 218 to 220 can be smaller than those in the vertical filter, and the latches 223 and 226 can replace the memories for one line, which obtain the sum totals. In this manner, the horizontal filter can be implemented with a smaller circuit scale.

When a material is sprayed onto the surface of a developing sleeve as a work, a moderate undulation forms on its coating, and even if that surface undulation is a small defect, such defect adversely influences image quality. For this reason, the vertical filter detects multi-valued digital data in units of pixels corresponding to the surface shape in the vertical direction, and then detects multi-valued digital data in units of pixels corresponding to the surface shape in the horizontal direction, thus reliably detecting undulations in the vertical and horizontal directions.

Figure 5:
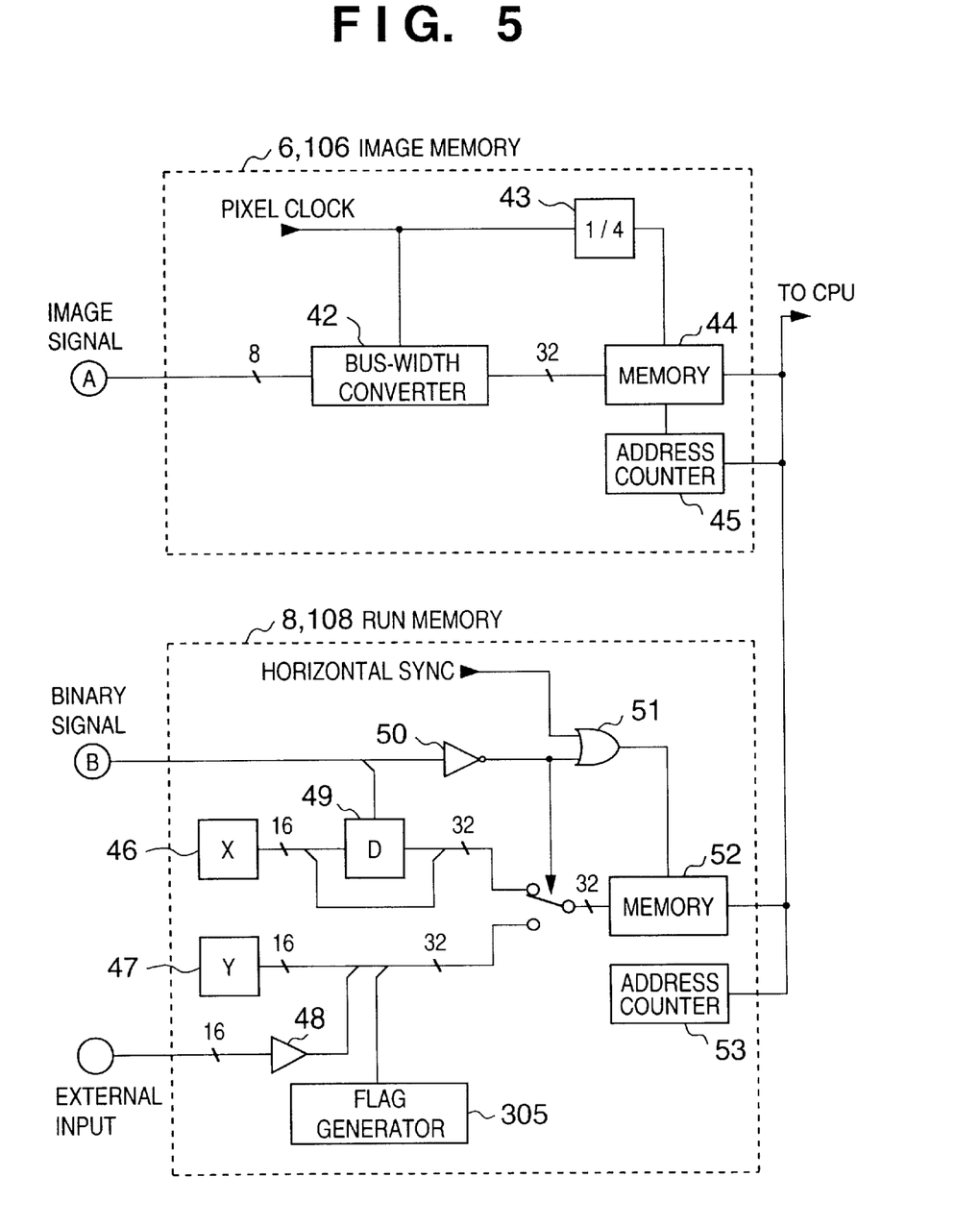
FIG. 5 is a block diagram of an image memory and run memory in FIG. 1.

FIG. 5 shows details of the image memory and run memory shown in FIG. 1.

As shown in FIG. 5, reference numeral 43 denotes a counter for frequency-dividing the clock frequency; 42, a bus-width converter for combining four 8-bit data to convert them into 32-bit data; 44 and 52, memories; 45 and 53, address counters which are incremented every time data is recorded; 46, a main scan coordinate counter which is incremented by a pixel clock; 47, a sub-scan coordinate counter which is incremented by a horizontal period; 48, a signal buffer for an external input; 49, a coordinate data latch; 50, an inverter for inverting the signal logic; and 51, an OR gate. Reference numeral 305 denotes a flag generator which generates flag values that are assigned different values to discriminate if the recording contents of the run memory are main scan coordinate data, sub-scan coordinate data, or an end mark.

Since an image signal of multi-valued digital data output from the horizontal filter is 8-bit data of 10 MHz, such data are combined in units of 4 bytes by the bus width converter 42 to obtain 32-bit data, and the 32-bit data are written in turn in the 32-bit memory 44 at addresses designated by the address counter 45 in response to clocks frequency-divided by the counter 43.

The binary signal (run code) output from the binary converter 7 sequentially writes the value of the counter 46 which is a horizontal coordinate X, and the value of the counter 47 which is a vertical coordinate Y in the 32-bit memory 52 as 32-bit data. As the write timings, a group of X-coordinates of points where the run code changes from 0 to 1, and a group of X-coordinates of points where the run code changes from 1 to 0 are sequentially written in the memory 52 in units of runs. Also, the Y-coordinate is written in the memory 52 together with a flag generated by the flag generator 305, which distinguishes the X- and Y-coordinates from each other, only when the current line includes a run.

Since 8-bit data input to the image memory undergo bus-width conversion into 32 bits, the write cycle in the memory can be prolonged to four times, and inexpensive memory elements can be used.

On the other hand, the values of the coordinate counters 46 and 47 are recorded in the run memory 52 in accordance with change points of the binary signal. The value of the main scan coordinate counter 46 is temporarily stored in the coordinate data latch 49 in response to the leading edge of the binary signal. The stored coordinate data and the current main scan coordinate data are then recorded in the run memory 52 in response to the trailing edge of the binary signal. As for the sub-scan coordinate value, if at least one run is detected from the scan line of interest, a sub-scan coordinate write flag (not shown) is set, and the sub-scan coordinate data, externally input bit pattern, and the value of the flag generator 305 are recorded.

With the aforementioned circuit operation, the run codes according to the binary determination result of a predetermined area to be inspected and multi-valued digital data can be stored in the memories 6 and 8. The control computer 9 can freely access these memory data.

These memory data undergoes a software process by the control computer 9.

The control computer 9 computes the feature amount of the binary signal in units of run codes. That is, the computer 9 reads out the contents of the run memory 8 from its start address, i.e., reads out X-coordinates until a flag indicating a Y-coordinate is found, and stores them in a line memory (not shown). Since all the X-coordinates stored in the line memory are located on a line indicated by the found Y-coordinate, the two-dimensional coordinates on the area to be inspected can be determined. Then, the computer 9 reads out multi-valued digital data corresponding to the run range from the image memory, computes the maximum and minimum values and the number of pixels of the readout data, and stores them as run attribute values in a line memory array together with the coordinate values. The computer 9 repeats such process for all the run codes stored in the run memory 8.

The control computer 9 then refers to the run codes and their attributes stored in the line memory array, and labels run codes that neighbor in the horizontal and vertical directions of the area to be inspected as a group of defects. Run codes which neighbor in the horizontal and vertical directions at a predetermined spacing or less are determined as neighboring ones in place of so-called four or eight neighbors which are normally used. When a defect like waste thread is formed on the surface upon coating of the developing sleeve, intermittent binary signals are generated since that defect has an elongated shape. With this embodiment, since such signals can be determined as a single defect, an inspection result that accurately determines an actual defect state can be obtained.

The control computer compares this inspection result with a given prescribed value to determine OK/NG, and outputs the determination result to the host sequencer.

According to the first embodiment, a required defect can be emphasized by two-dimensional filtering, and can be easily detected.

Even when the product to be inspected is a photosensitive drum, although the detection signal moderately fluctuates due to illumination nonuniformity upon inspecting the surface coating, or a slight offset of a clamp shaft upon inspection, the influences of such fluctuations can be removed, and a defect alone can be emphasized, thus improving the detection precision.

When the work is a charging roller, paper feed roller, or the like having a rough surface, variations of the background can be smoothed by strengthening the smoothing effect, thus improving the detection sensitivity.

For dust on a liquid crystal display board, dedicated printing paper, or the like, two-dimensional filters that can avoid the influences of nonuniformity of illumination light or the like as in this embodiment function effectively, thus improving the defect detection sensitivity of dust, scratches, and the like.

Second Embodiment

A defect information processing apparatus of the second embodiment will be explained below with reference to FIGS. 6A and 6B.

Figure 6A:
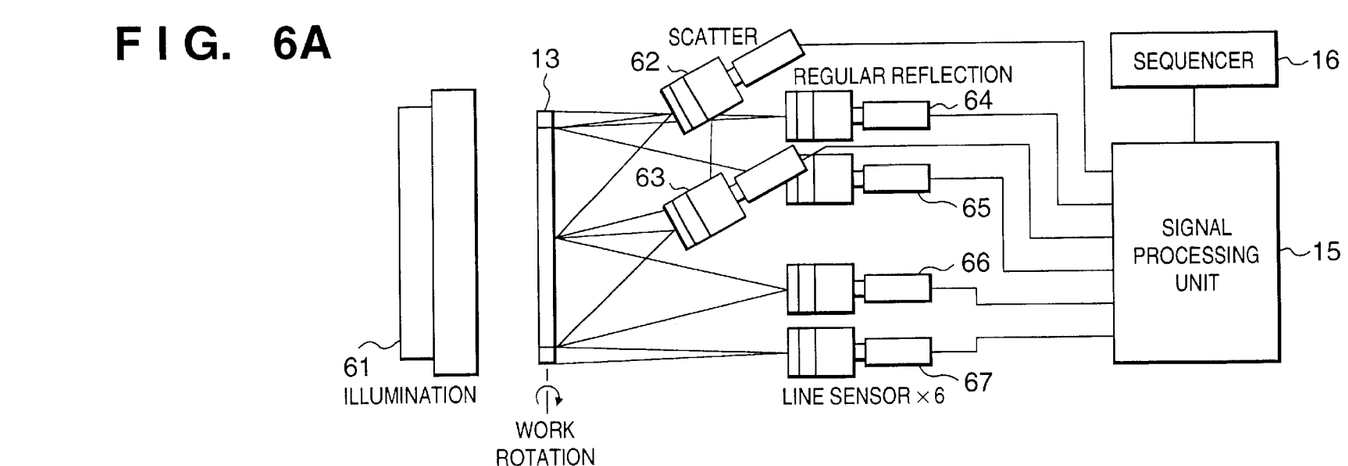
FIG. 6A is a view showing the system arrangement of a defect information processing apparatus according to the second embodiment of the present invention.

FIG. 6A shows the system arrangement of a defect information processing apparatus according to the second embodiment of the present invention. FIG. 6B is a side view of FIG. 6A.

Figure 6B:
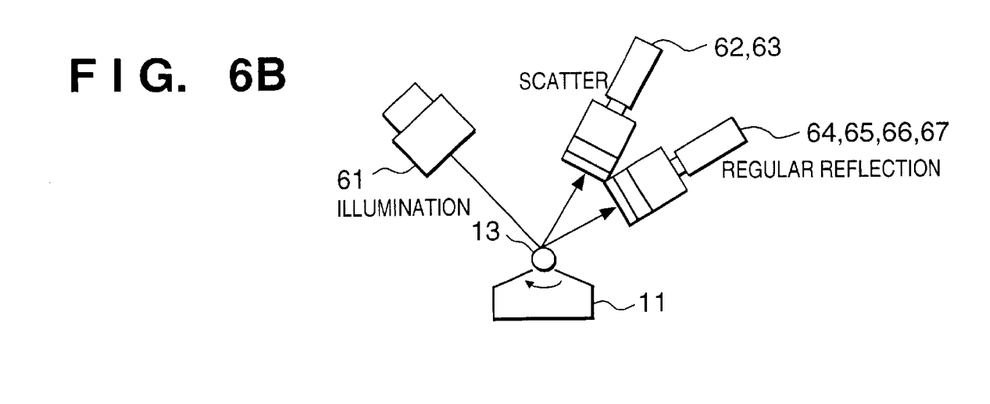
FIG. 6B is a side view of FIG. 6A.

As shown in FIGS. 6A and 6B, reference numeral 61 denotes an illumination device that illuminates the overall work; and 62 to 67, line sensor cameras, which receive light reflected by the work within their field ranges. Reference numeral 15 denotes a signal processing unit for receiving analog signals detected by the cameras 62 to 67 in units of cameras.

In this manner, by increasing the number of line sensors, the resolution of the area to be inspected can be improved. Also, since light components regularly reflected by the work and those scattered thereby are received by different line sensors, the number of kinds of defects that can be detected can be increased, thus assuring higher quality guarantee.

In the second embodiment, the signal processing unit 15 includes circuits corresponding to one channel shown in FIG. 1 in correspondence with the number of line sensors (six systems in this embodiment).

The arrangement and operation of the signal processing unit 15 are the same as those in the first embodiment, and the maximum and minimum values, areas, coordinates, and the like can be obtained in units of defect data.

As described above, according to this embodiment, the vertical filter can emphasize a defect signal by executing a linear filter process such as smoothing, differentiation, or the like of multi-valued digital data in the sub-scan direction. On the other hand, the horizontal filter can emphasize a defect signal by executing a linear filter process such as smoothing, differentiation, or the like of multi-valued digital data in the ma in scan direction.

The binary converter can remove an isolated pixel, and can couple pixels which neighbor but are nonetheless separated so as to drop the spatial frequency of a binary signal.

The vertical and horizontal filters can reduce random noise components and high-frequency components, and improve the S/N ratio of the detection signal by computing the difference values of multi-valued digital data within a predetermined range to reduce the range to be averaged to a size as small as a defect to be detected.

The vertical and horizontal filters can extract only undulation components by computing the difference values of multi-valued digital data within another range, and averaging a range as small as large undulation components of the detection signal due to a mechanical wobble, warp, and the like of the work.

The vertical and horizontal filter can emphasize and extract a signal of a defect to be detected by subtracting undulation components from the detection signal, the S/N ratio of which has been improved by weighting the two difference values and computing the difference between these weighted difference values.

The binary converter executes a dilation process which sets predetermined pixel values that neighbor a pixel with a pixel value="1" to be "1" to couple pixel values="1" which neighbor but are nonetheless separated by setting pixel values between those pixel values to be "1".

Also, the binary converter executes an erosion process which sets a predetermined pixel that neighbors a pixel with a pixel value="0" to be "0", thus removing an isolated pixel with a pixel value="1". When data that has undergone the dilation process undergoes the erosion process, a set of neighboring pixel values="1" remain without being removed, and isolated pixels with a pixel value="1" at a predetermined pixel sp acing or more are removed.

Therefore, even for a defect that changes slightly in the main scan direction, a large detection signal can be obtained by providing digital filters having large numbers of taps in the horizontal and vertical directions.

By satisfying th e required filter function while suppressing the circuit scale of the filter process in the main scan direction, the defect detection performance can be improved, and the apparatus cost can be reduced.

Furthermore, by prolonging the interval between neighboring change points of the binary signal and assuring a sufficiently long write time of the coordinate values of run code s in th e memory, a low-speed memory can be used, and the apparatus cost can be reduced.

Other Embodiment

The present invention is also achieved by supplying a storage medium, which records a program code of a software program that can implement the functions of the above-mentioned embodiments to the system or apparatus, and reading out and executing the program code stored in the storage medium by a computer (or a CPU or MPU) of the system or apparatus.

In this case, the program code itself read out from the storage medium implements the functions of the above-mentioned embodiments, and the storage medium which stores the program code constitutes the present invention.

As the storage medium for supplying the program code, for example, a floppy disk, hard disk, optical disk, magneto-optical disk, CD-ROM, CD-R, magnetic tape, nonvolatile memory card, ROM, and the like may be used.

The functions of the above-mentioned embodiments may be implemented not only by executing the readout program code by the computer but also by some or all of actual processing operations executed by an OS (operating system) running on the computer on the basis of an instruction of the program code.

Furthermore, the functions of the above-mentioned embodiments may be implemented by some or all of actual processing operations executed by a CPU or the like arranged in a function extension board or a function extension unit, which is inserted in or connected to the computer, after the program code read out from the storage medium is written in a memory of the extension board or unit.

When the present invention is applied to the storage medium, a program code corresponding to the aforementioned flow chart is stored in that storage medium.

The present invention is not limited to the above embodiments and various changes and modifications can be made within the spirit and scope of the present invention. Therefore, to apprise the public of the scope of the present invention the following claims are made.

What is claimed is:

1. A defect information processing apparatus comprising:
   image input means for capturing a two-dimensional image of an object to be inspected;
   digital conversion means for converting the two-dimensional image into multi-valued digital image data;
   vertical filter means for filtering the multi-valued digital image data in a vertical direction;
   horizontal filter means for filtering the multi-valued digital image data, which has been filtered by said vertical filter means, in a horizontal direction;
   binarization means for converting the multi-valued digital image data, which has been filtered by said horizontal filter means, into binary data on the basis of a predetermined reference value; and
   detection means for detecting a defect portion of the object to be inspected on the basis of the multi-valued digital image data and binary data, wherein said vertical filter means comprises vertical difference computation means for computing a difference value of the multi-valued digital image data within a predetermined range in the vertical direction, and vertical weighting means for weighting the difference value computed by said vertical difference computation means, and said horizontal filter means comprises horizontal difference computation means for computing a difference value of the multi-valued digital image data within a predetermined range in the horizontal direction, and horizontal weighting means for weighting the difference value computed by said horizontal difference computation means.

2. The apparatus according to claim 1, wherein said vertical difference computation means comprises first vertical difference computation means for computing a difference value of the multi-valued digital data within a first range in the vertical direction, and second vertical difference computation means for computing a difference value of the multi-valued digital data within a second range in the vertical direction, and said vertical weighting means comprises first vertical weighting means for weighting the difference value computed by said first vertical difference computation means, and second vertical weighting means for weighting the difference value computed by said second vertical difference computation means, and said vertical difference computation means further comprises third vertical difference computation means for computing a difference between the difference values weighted by said first and second vertical weighting means.

3. The apparatus according to claim 1, wherein said horizontal difference computation means comprises first horizontal difference computation means for computing a difference value of the multi-valued digital data within a first range in the horizontal direction, and second horizontal difference computation means for computing a difference value of the multi-valued digital data within a second range in the horizontal direction, and said horizontal weighting means comprises first horizontal weighting means for weighting the difference value computed by said first horizontal difference computation means, and second horizontal weighting means for weighting the difference value computed by said second horizontal difference computation means, and said horizontal difference computation means further comprises third horizontal difference computation means for computing a difference between the difference values weighted by said first and second horizontal weighting means.

4. The apparatus according to claim 1, wherein said apparatus comprises a plurality of filter means each including said vertical and horizontal filter means, and further comprises switch means for switching a connection of said filter means to a series or parallel connection.

5. The apparatus according to claim 1, wherein said vertical and horizontal weighting means comprise multipliers or barrel shifters which respectively multiply the difference values computed by said vertical and horizontal difference computation means by predetermined factors.

6. The apparatus according to claim 1, wherein said image input means comprises a photosensor for capturing light which strikes a surface to be inspected of the object to be inspected, and is reflected by the surface to be inspected.

7. The apparatus according to claim 1, wherein the object to be inspected is a photosensitive drum.

8. The apparatus according to claim 1, wherein the object to be inspected is a developing sleeve.

9. The apparatus according to claim 1, wherein the object to be inspected is a charging roller.

10. The apparatus according to claim 1, wherein the object to be inspected is a printing paper feed roller.

11. The apparatus according to claim 1, wherein the object to be inspected is a liquid crystal display board.

12. The apparatus according to claim 1, wherein the object to be inspected is printing paper.

13. A defect information processing method comprising:

the image input step of capturing a two-dimensional image of an object to be inspected;

the digital conversion step of converting the two-dimensional image into multi-valued digital image data;

the vertical filter step of filtering the multi-valued digital image data in a vertical direction;

the horizontal filter step of filtering the multi-valued digital image data, which has been filtered in the vertical filter step, in a horizontal direction;

the binarization step of converting the multi-valued digital image data, which has been filtered in the horizontal filter step, into binary data on the basis of a predetermined reference value; and the detection step of detecting a defect portion of the object to be inspected on the basis of the multi-valued digital image data and binary data, wherein the vertical filter step comprises the vertical difference computation step of computing a difference value of the multi-valued digital image data within a predetermined range in the vertical direction, and the vertical weighting step of weighting the difference value computed in the vertical difference computation step, and the horizontal filter step comprises the horizontal difference computation step of computing a difference value of the multi-valued digital image data within a predetermined range in the horizontal direction, and the horizontal weighting step of weighting the difference value computed in the horizontal difference computation step.

14. The method according to claim 13, wherein the vertical difference computation step comprises the first vertical difference computation step of computing a difference value of the multi-valued digital data within a first range in the vertical direction, and the second vertical difference computation step of computing a difference value of the multi-valued digital data within a second range in the vertical direction, and the vertical weighting step comprises the first vertical weighting step of weighting the difference value computed in the first vertical difference computation step, and the second vertical weighting step of weighting the difference value computed in the second vertical difference computation step, and the vertical difference computation step further comprises the third vertical difference computation step of computing a difference between the difference values weighted in the first and second vertical weighting steps.

15. The method according to claim 13, wherein the horizontal difference computation step comprises the first horizontal difference computation step of computing a difference value of the multi-valued digital data within a first range in the horizontal direction, and the second horizontal difference computation step of computing a difference value of the multi-valued digital data within a second range in the horizontal direction, and the horizontal weighting step comprises the first horizontal weighting step of weighting the difference value computed in the first horizontal difference computation step, and the second horizontal weighting step of weighting the difference value computed in the second horizontal difference computation step, and the horizontal difference computation step further comprises the third horizontal difference computation step of computing a difference between the difference values weighted in the first and second horizontal weighting steps.

16. The method according to claim 13, wherein said method comprises a plurality of filter steps each including the vertical and horizontal filter steps, and a connection of the filter steps can be switched to a series or parallel connection.

17. The method according to claim 13, wherein the image input step includes the step of capturing the two-dimensional image of the object to be inspected using a photosensor for capturing light which strikes a surface to be inspected of the object to be inspected, and is reflected by the surface to be inspected.

18. The method according to claim 13, wherein the object to be inspected is a photosensitive drum.

19. The method according to claim 13, wherein the object to be inspected is a developing sleeve.

20. The method according to claim 13, wherein the object to be inspected is a charging roller.

21. The method according to claim 13, wherein the object to be inspected is a printing paper feed roller.

22. The method according to claim 13, wherein the object to be inspected is a liquid crystal display board.

23. The method according to claim 13, wherein the object to be inspected is printing paper.

24. A computer readable memory that stores a program code which comprises codes of the image input step of capturing a two-dimensional image of an object to be inspected, the digital conversion step of converting the two-dimensional image into multi-valued digital image data, the vertical difference computation step of computing a difference value of the multi-valued digital image data within a predetermined range in the vertical direction, the vertical weighting step of weighting the difference value computed in the vertical difference computation step, the horizontal difference computation step of computing a difference value of the multi-valued digital image data within a predetermined range in the horizontal direction, the horizontal weighting step of weighting the difference value computed in the horizontal difference computation step, and the detection step of detecting a defect portion of the object to be inspected on the basis of the multi-valued digital image data and binary data, which is generated via the binarization step of converting the multi-valued digital image data, which has been computed via the horizontal weighting step, into binary data on the basis of a predetermined reference value, and processes defect information of the object to be inspected, comprising:

a code of the step of computing feature data of a pixel which corresponds to the binary data=1; and a code of determining based on the feature data if the object to be inspected is good.

* * * * *

UNITED STATES PATENT AND TRADEMARK OFFICE
CERTIFICATE OF CORRECTION

PATENT NO. : 6,643,395 B1
DATED : November 4, 2003
INVENTOR(S) : Masaharu Okabe

It is certified that error appears in the above-identified patent and that said Letters Patent is hereby corrected as shown below:

Column 1,
Line 19, "very" should be deleted.

Column 5,
Line 14, "form" should read -- from --;
Line 36, "arbitrary" should read -- arbitrarily --; and
Line 43, "in" should read -- in a --.

Column 6,
Line 20, "that" should read -- that of --; and
Line 61, "mounts" should read -- amounts --.

Column 7,
Line 62, "mounts" should read -- amounts --.

Column 8,
Line 19, "with" should read -- width --.

Column 10,
Line 1, "undergoes" should read -- undergo --.

Column 11,
Line 27, "ma in" should read -- main --; and
Line 62, "sp acing" should read -- spacing --.

UNITED STATES PATENT AND TRADEMARK OFFICE
CERTIFICATE OF CORRECTION

PATENT NO. : 6,643,395 B1
DATED : November 4, 2003
INVENTOR(S) : Masaharu Okabe It is certified that error appears in the above-identified patent and that said Letters Patent is hereby corrected as shown below:

<u>Column 12,</u>
Line 1, "th e" should read -- the --; and
Line 8, "code s in th e" should read -- codes in the --.

Signed and Sealed this

Fourteenth Day of February, 2006

JON W. DUDAS
*Director of the United States Patent and Trademark Office*